US00PP15224P2

(12) United States Plant Patent
Dümmen

(10) Patent No.: US PP15,224 P2
(45) Date of Patent: Oct. 12, 2004

(54) **VARIETY OF *BEGONIA* PLANT NAMED 'BBVERONICA'**

(50) Latin Name: *Begonia elatior*
Varietal Denomination: BBVeronica

(75) Inventor: Tobias Günter Dümmen, Rheinberg (DE)

(73) Assignee: Begonia Breeders Association B.V. (NL)

( * ) Notice: Subject to any disclaimer, the term of this patent is extended or adjusted under 35 U.S.C. 154(b) by 0 days.

(21) Appl. No.: 10/409,943

(22) Filed: Apr. 9, 2003

(51) Int. Cl.[7] ..... A01H 5/00
(52) U.S. Cl. ..... Plt./349
(58) Field of Search ..... Plt./349

(56) References Cited

U.S. PATENT DOCUMENTS

PP4,781 P * 10/1981 Mikkelsen et al. ..... Plt./349
PP5,391 P * 1/1985 Schelbeck ..... Plt./349
PP5,532 P * 8/1985 Mikkelsen ..... Plt./349

OTHER PUBLICATIONS

UPOV ROM GTITM Computer Database, GTI Jouve Retrieval Software 2003/04 Citation for 'BBVeronica'.*

* cited by examiner

*Primary Examiner*—Bruce R. Campell
*Assistant Examiner*—W C Haas
(74) *Attorney, Agent, or Firm*—Webb Ziesenheim Logsdon Orkin & Hanson, P.C.

(57) ABSTRACT

A new and distinct early flowering *Begonia* plant with dark red colored flowers.

1 Drawing Sheet

Botanical classification: *Begonia elatior.*
Varietal denomination: 'BBVERONICA'.

BACKGROUND OF THE INVENTION

The present invention comprises a new and distinct cultivar of *Begonia* plant known by the varietal name 'BBVeronica'. The new variety was discovered in 1999 in a selected breeding program in Aalsmeer, Netherlands. The new variety is a color mutation of 'Line' (unpatented parent). The new variety has a shape and vigor similar to its parent, but differs in flower color and rate of opening from its parent. The new variety was first asexually reproduced in 1999 by cuttings in Aalsmeer, Netherlands. The new variety has been trial and field tested at Aalsmeer and has been found to retain its distinctive characteristics and remain true to type through successive propagations.

The following traits distinguish 'BBVeronica' as a new and distinct cultivar:

1. The flower color is dark red.
2. The flower exhibits better opening.

DESCRIPTION OF THE DRAWINGS

The accompanying photographic drawing illustrates the new variety, with the color being as nearly true as is possible with color illustrations of this type.

DESCRIPTION OF THE PLANT

Figure 1:
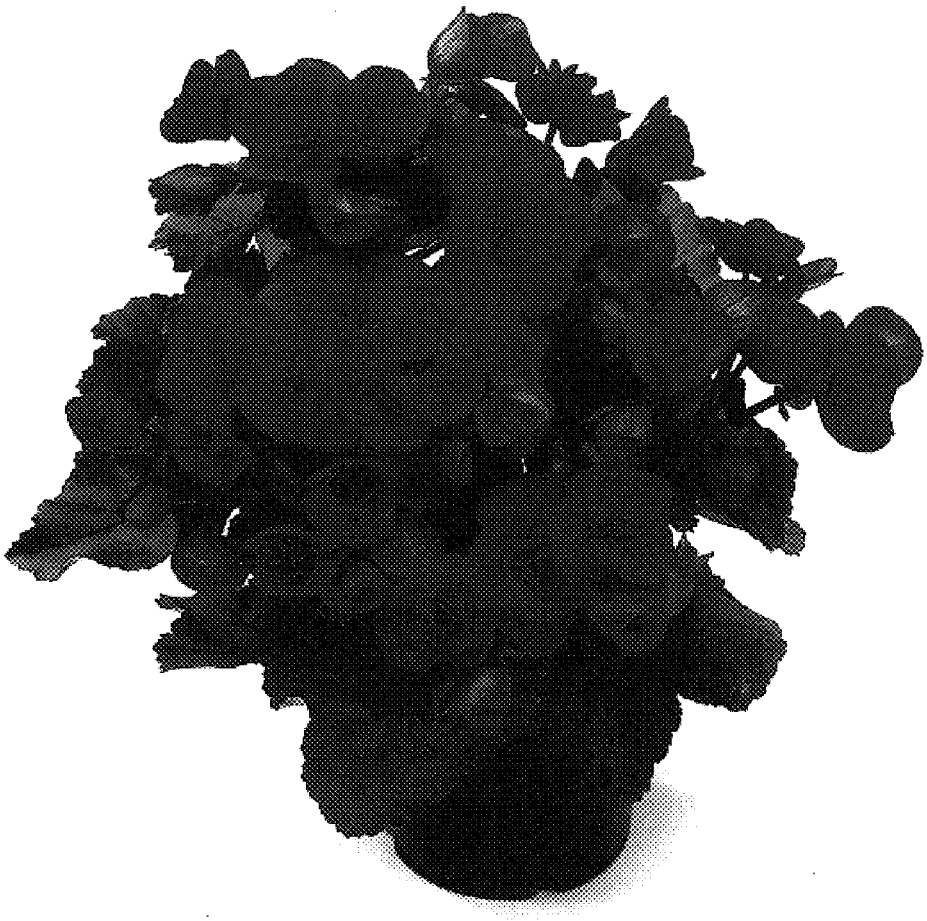

The following detailed description sets forth characteristics of the new cultivar. The data which defines these characteristics were collected by asexual reproductions by cuttings carried out in Aalsmeer, Netherlands. The plants were cultivated in a greenhouse having an average temperature of 20° C. Plants for the description were 12 weeks old and in 13 cm containers. The color readings were taken in a shaded greenhouse under natural light in the summer. Color references are primarily to The 2001 R.H.S. Colour Chart of The Royal Horticultural Society of London.

PLANT

Form: Upright; compact.
Height:
*Media surface to top of leaves.*—18 cm.
*Media surface to top of flowers.*—22 cm.
Width: 25 cm.
Lateral branches:
*Number.*—4–5.
*Color.*—145A.
*Length.*—15 cm.
*Diameter.*—1.3 cm.
*Texture.*—Smooth.
*Internode length.*—1–3 cm.
Foliage:
*Arrangement.*—Alternate.
*Quantity.*—6 per lateral branch.
*Length.*—9 cm.
*Width.*—8 cm.
*Shape.*—Asymmetrical ovate.
*Apex.*—Acuminate.
*Base.*—Oblique.
*Margin.*—Crenate.
*Texture.*—Smooth-velvety.
*Color.*—Upper surface: 139A. Lower surface: 137C. Anthocyanin: 54B.
*Petiole.*—Diameter: 4 mm. Color: 145A.
*Stipule.*—Quantity: 2 per leaf, 1 cm. Shape: Asymmetrical; pointed. Apex: Acute. Base: Straight. Margin: Entire. Color: Upper surface: 139B. Lower surface: 139C.
*Venation.*—Upper surface: 139B. Lower surface: 139C.

FLOWER

Natural flowering season: Year round; continuous.
Flowering longevity on the plant: 4 weeks.
Flowers:
*Arrangement.*—Compound; not aborted.
*Cyme diameter.*—7–8 cm.
*Number of flowers per cyme.*—5–6.
*Aspect.*—Flat to cupped.
*Shape.*—Oval; round.
*Diameter.*—5 cm.
*Height.*—1 cm.
*Fragrance.*—None.
*Number of flowers per plant.*—30.
Bud:
*Shape.*—Oval.
*Diameter.*—2 cm.
*Length.*—1.5 cm.
*Color.*—44A.
*Rate of flower opening.*—3–4 days.
Petals:
*Arrangement.*—Double.
*Shape.*—Rounded; obovate.
*Apex.*—Rounded.
*Base.*—Cordate.
*Margin.*—Entire.
*Quantity.*—10–18 per flower.
*Size.*—Length: 3 cm. Width: 4 cm.
*Texture.*—Smooth.
*Color.*—Upper surface: 42A. Lower surface: 42B.
Peduncles:
*Angle.*—30–45° from vertical.
*Strength.*—Strong.
*Length.*—5–6 cm.
*Diameter.*—0.5 cm.
*Color.*—30C.
Pedicels:
*Angle.*—30–45° from vertical.
*Strength.*—Strong.
*Length.*—2–3 cm.
*Diameter.*—0.2 cm.
*Color.*—30C.
Bracts:
*Arrangement.*—Opposite.
*Shape.*—Broadly cordate.
*Apex.*—Acute.
*Margin.*—Entire.
*Length.*—1.2 cm.
*Width.*—1.5 cm.
*Color.*—Upper surface: 41A. Lower surface: 41A.
Reproductive organs: None.
Disease resistance: Resistant to mildew.
Seed production: None.

I claim:

1. A new and distinct variety of *Begonia* plant substantially as shown and described.

* * * * *